US009143864B2

(12) United States Patent
Pan

(10) Patent No.: US 9,143,864 B2
(45) Date of Patent: Sep. 22, 2015

(54) AUDIO PLAYBACK SYSTEM

(71) Applicant: Primax Electronics Ltd., Neihu, Taipei (TW)

(72) Inventor: Yung-Tai Pan, Taipei (TW)

(73) Assignee: PRIMAX ELECTRONICS LTD., Taipei (TW)

( * ) Notice: Subject to any disclaimer, the term of this patent is extended or adjusted under 35 U.S.C. 154(b) by 141 days.

(21) Appl. No.: 14/107,392

(22) Filed: Dec. 16, 2013

(65) Prior Publication Data

US 2015/0036830 A1 Feb. 5, 2015

(30) Foreign Application Priority Data

Aug. 5, 2013 (TW) ............................. 102127943 A

(51) Int. Cl.

*H04R 5/00* (2006.01)
*A61F 11/06* (2006.01)
*G10K 11/16* (2006.01)
*H03B 29/00* (2006.01)
*H04R 5/04* (2006.01)
*H04S 1/00* (2006.01)

(52) U.S. Cl.

CPC .. *H04R 5/04* (2013.01); *H04S 1/007* (2013.01)

(58) Field of Classification Search

CPC ........... H04S 7/30; H04S 7/305; H04S 7/308; H04S 7/307; H04R 5/04; H04M 1/7253; H04M 2250/02

USPC ............. 381/26, 17, 107, 1, 71.11, 71.6, 398; 455/41.2, 575.2

See application file for complete search history.

(56) References Cited

U.S. PATENT DOCUMENTS 7,146,191 B2 * 12/2006 Kerner et al. ................. 455/558
8,131,905 B2 * 3/2012 Rofougaran .................. 710/303

* cited by examiner

*Primary Examiner* — Thjuan K Addy

(74) *Attorney, Agent, or Firm* — Kirton McConkie; Evan R. Witt

(57) ABSTRACT

An audio playback system includes a handheld device and a digital stereo set. By the handheld device, a control message is converted into a modulation signal. The modulation signal is transmitted to a speaker, thereby controlling the speaker to generate a modulated sound wave signal. After the modulated sound wave signal is received by a built-in microphone of the digital stereo set, the modulated sound wave signal is restored to the control message. After the control message is received by the digital stereo set, the digital stereo set performs a corresponding control action.

13 Claims, 7 Drawing Sheets

AUDIO PLAYBACK SYSTEM

FIELD OF THE INVENTION

The present invention relates to an audio playback system, and more particularly to an audio playback system including a handheld device and a digital stereo set.

BACKGROUND OF THE INVENTION

Conventionally, a digital stereo set is controlled by using a control panel or a remote controller. As known, the control panel or the remote controller can only provide basic control items, and the control panel or the remote controller can not be personalized. With increasing development of science and technology, the functions of the current handheld devices such as smart phones or tablet personal computers become very complete. Moreover, the current handheld devices have diversified controllable items and can perform personalized control actions. Consequently, it is an important issue to research how to use the handheld device to control the digital stereo set.

Nowadays, the handheld device may be in communication with the digital stereo set by a wireless communication technology in order to control the digital stereo set. The wireless communication technology widely used in the handheld device is for example a Wi-Fi communication technology, a Bluetooth communication technology or a near field communication technology. Regardless of which wireless communication technology is adopted, both of the handheld device and the digital stereo set should be additionally equipped with corresponding chips. In other words, the use of the wireless communication technology is neither cost-effective nor user-friendly. For example, a Bluetooth pairing process is very complicated. In addition, the same Bluetooth device fails to be operated by many handheld devices simultaneously. Moreover, since the above-mentioned wireless communication technologies belong to radio frequency communication technologies, the generated electromagnetic radiation is detrimental to human health, and a problem of electromagnetic radiation channel occupancy occurs.

Therefore, there is a need of providing an improved communication and control method for a handheld device and a digital stereo set in order to eliminate the above drawbacks of the wireless communication and provide abundant personalized control actions.

SUMMARY OF THE INVENTION

The present invention relates to an audio playback system by using a handheld device to transmit a control message to a digital stereo set by sound wave.

In accordance with an aspect of the present invention, there is provided an audio playback system. The audio playback system includes a handheld device and a digital stereo set. The handheld device includes a first transmitting terminal controller. The first transmitting terminal controller includes a first speaker and a first sound wave signal generator. The first sound wave signal generator is used for converting a control message into a first modulation signal, and transmitting the first modulation signal to the first speaker, thereby controlling the first speaker to generate a first modulated sound wave signal. The digital stereo set includes a host and a sound box for playing a digital audio file. The digital stereo set further includes a first receiving terminal controller. The first receiving terminal controller includes a first microphone for receiving the first modulated sound wave signal and a first sound wave signal reader for restoring the first modulated sound wave signal to the control message. After the control message is received by the digital stereo set, the digital stereo set performs a corresponding control action according to the control message.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

Figure 1:
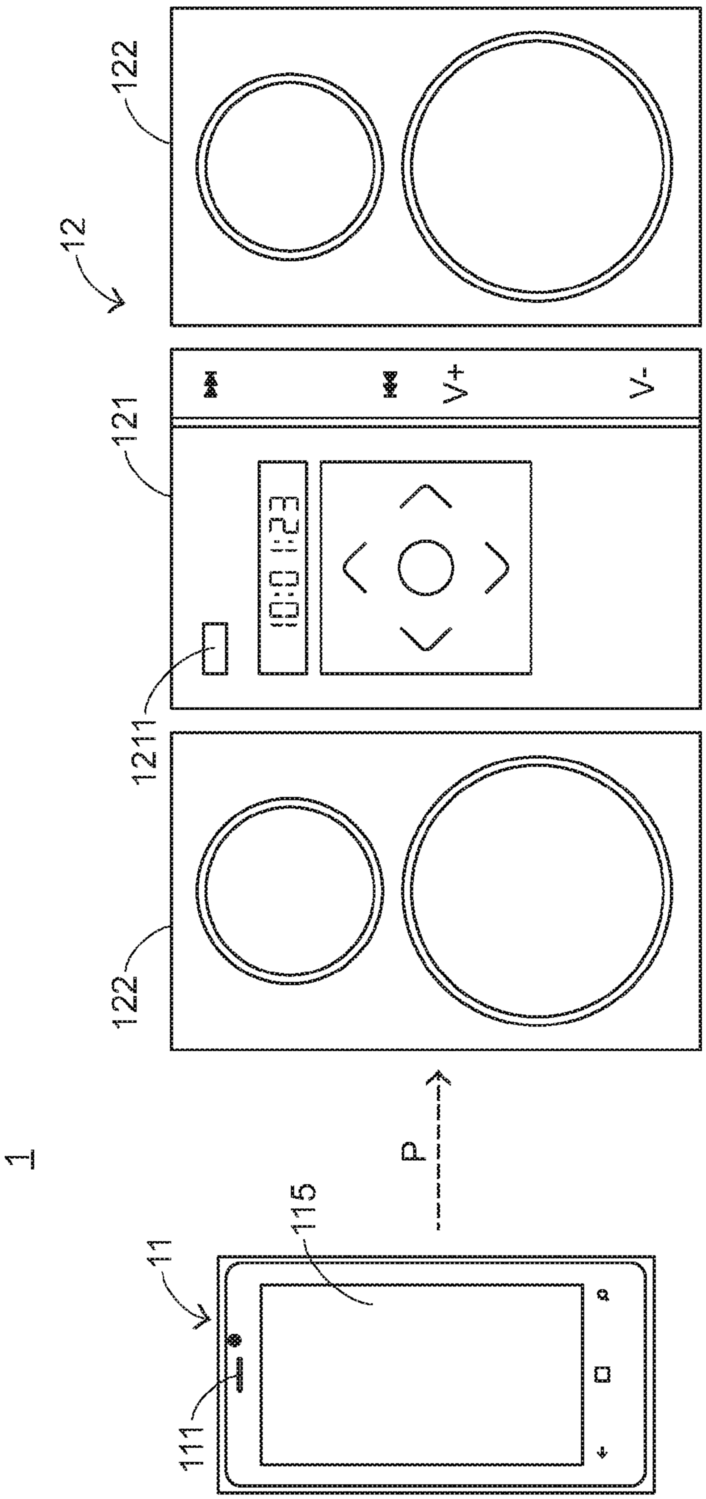
FIG. 1 schematically illustrates the architecture of an audio playback system according to a first embodiment of the present invention.

The present invention provides an audio playback system for eliminating the drawbacks of the prior art technology. First of all, the architecture of the audio playback system of the present invention will be illustrated as follows. FIG. 1 schematically illustrates the architecture of an audio playback system according to a first embodiment of the present invention. As shown in FIG. 1, the audio playback system 1 comprises a handheld device 11 and a digital stereo set 12.

In this embodiment, the handheld device 11 is a smart phone or a tablet personal computer. The smart phone or the tablet personal computer runs an operating system. An example of the operating system includes but is not limited to Android, iOS, BlackBerry OS, Windows Mobile, Windows Phone, bada OS or Symbian OS. It is noted that the handheld device 11 may be a smart phone or a tablet personal computer running any other appropriate operating system.

The digital stereo set 12 has the capability of playing digital audio files. The digital audio files denote the digitalized audio contents. For example, the digital audio files are WMA (Windows Media Audio) files, MP3 (MPEG Audio Layer 3) files, WAV (Waveform audio format) files or AAC (Advanced audio coding) files, but are not limited thereto. The digital stereo set 12 can also play other-format digital audio files.

The handheld device 11 comprises a first speaker 111. In this embodiment, the first speaker 111 is located at a front side of the handheld device 11. In particular, the first speaker 111 is used for hearing the person the user is taking to during a phone call. Alternatively, in some other embodiments, the first speaker may be located at a bottom or a rear side of the handheld device 11 for playing audio contents.

In this embodiment, the digital stereo set 12 comprises a host 121, at least one sound box 122, and a first microphone 1211. The first microphone 1211 is installed in the host 121. In this embodiment, the host 121 and the sound box 122 are separate components. Alternatively, in some other embodiments, the digital stereo set 12 is a single-box stereo set where the host 121 and the sound box 122 are integrated into an integral stereo set.

Moreover, an example of the first microphone 1211 includes but is not limited to a dynamic microphone, a capacitive microphone, an electret condenser microphone or a microelectromechanical systems (MEMS) microphone.

In the audio playback system 1 of this embodiment, a modulated sound wave signal from the first speaker 111 of the handheld device 11 may be received by the first microphone 1211 of the digital stereo set 12. According to the modulated sound wave signal, a control message from the handheld device 11 is obtained by the digital stereo set 12. Moreover, according to the control message, a control action is executed by the digital stereo set 12. The operations of the audio playback system 1 will be illustrated as follows.

Figure 2:
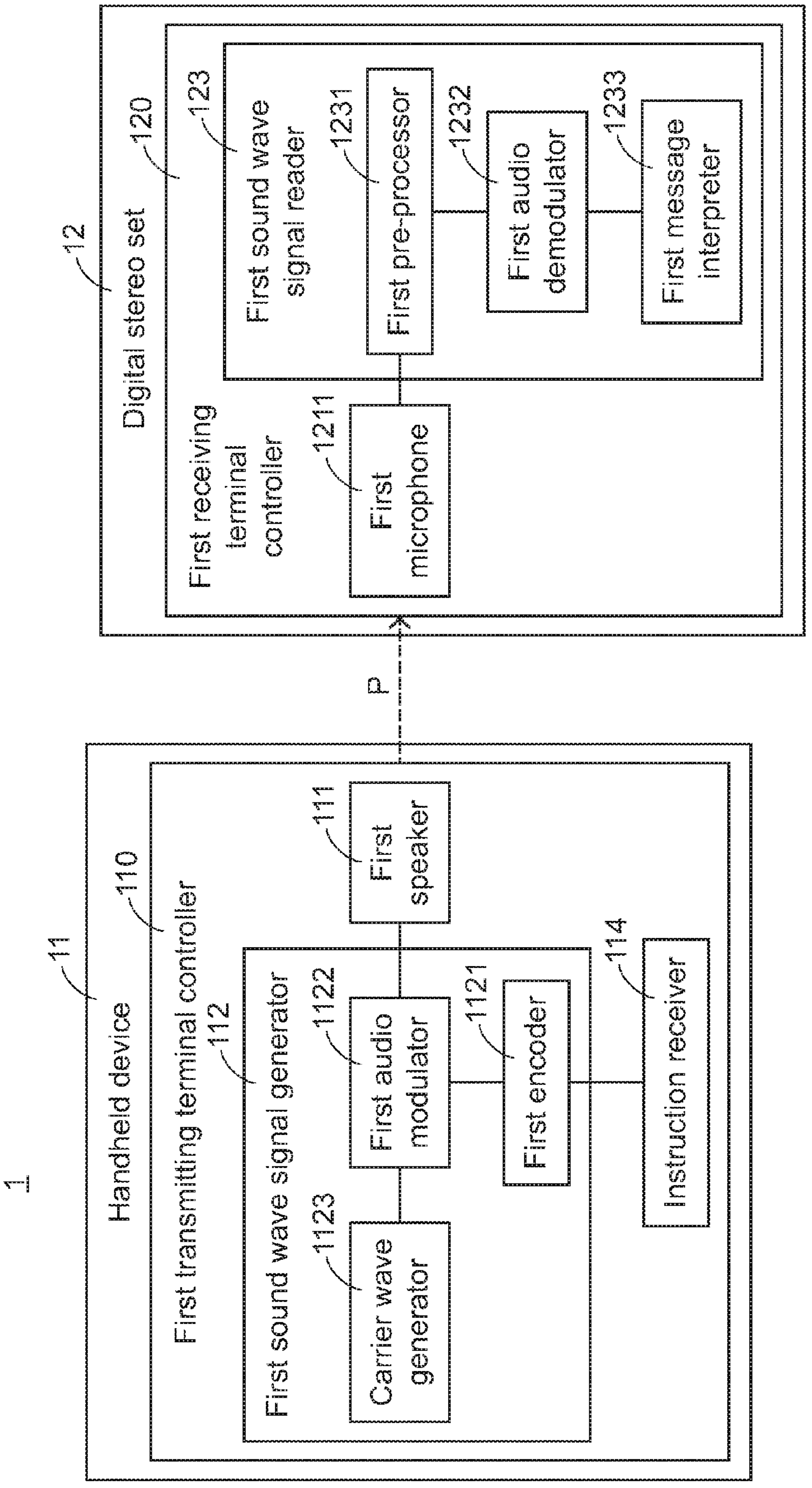
FIG. 2 is a schematic functional block illustrating the audio playback system according to the first embodiment of the present invention.
Figure 3:
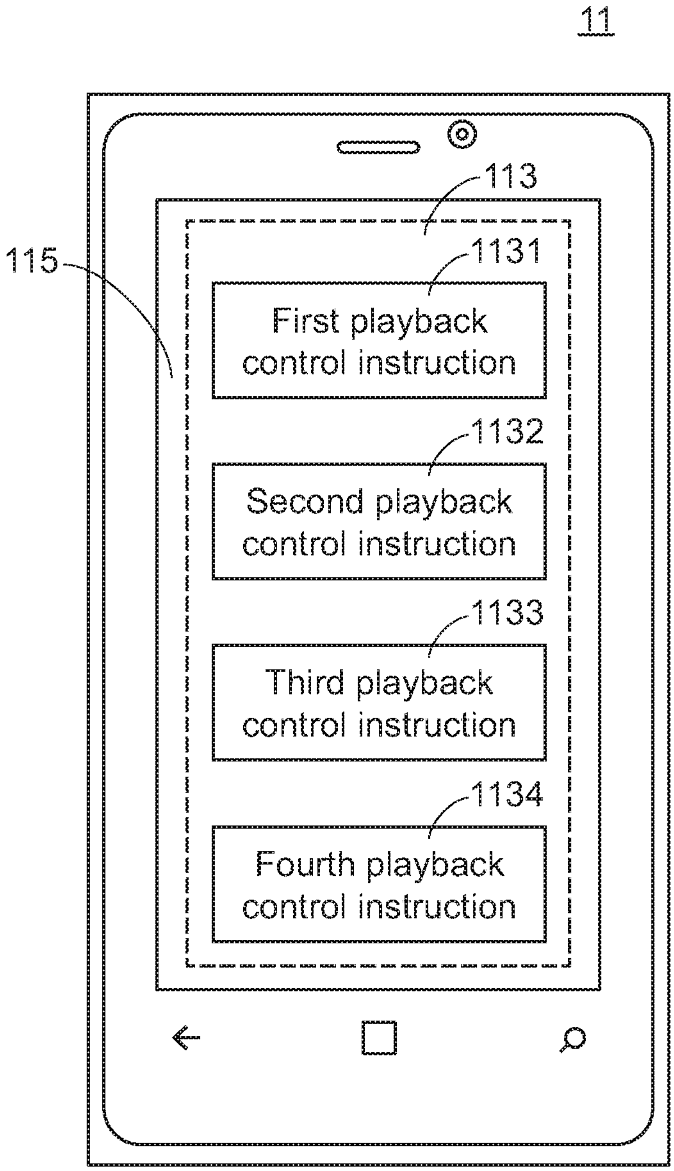
FIG. 3 schematically illustrates a user interface of the audio playback system according to the first embodiment of the present invention.
Figure 4:
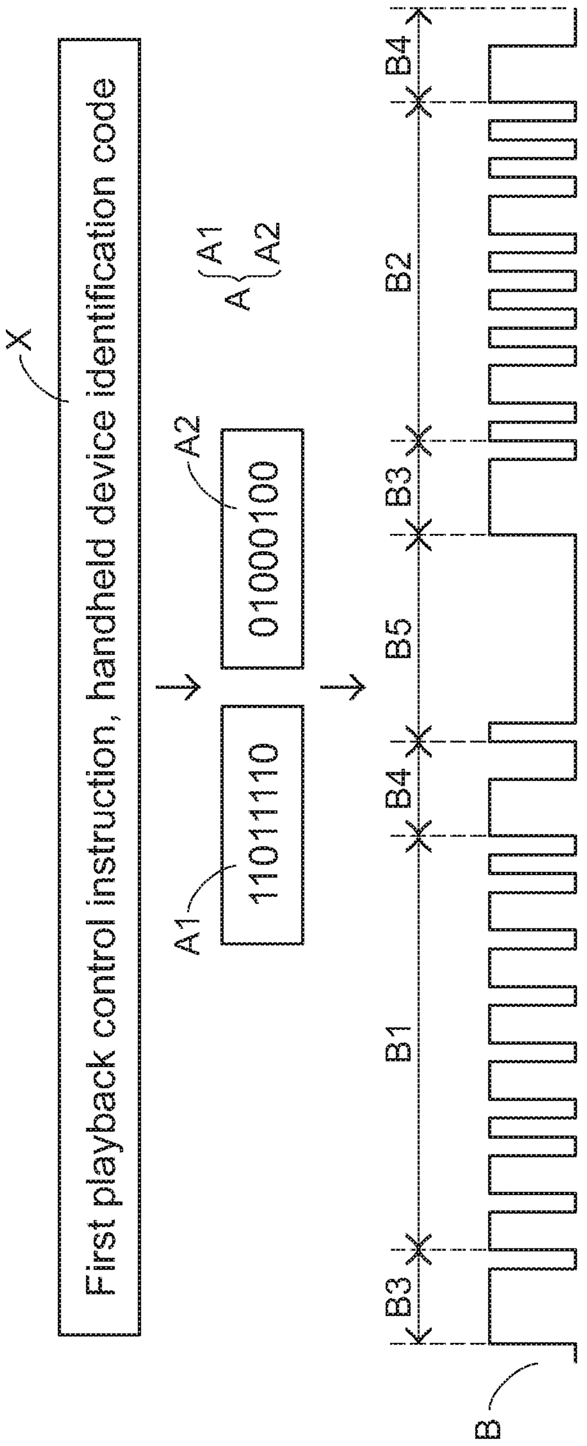
FIG. 4 schematically illustrates associated signals processed by the audio playback system according to the first embodiment of the present invention.

Hereinafter, the operations of the audio playback system 1 will be illustrated with reference to FIGS. 1-4. FIG. 2 is a schematic functional block illustrating the audio playback system according to the first embodiment of the present invention. FIG. 3 schematically illustrates a user interface of the audio playback system according to the first embodiment of the present invention. FIG. 4 schematically illustrates associated signals processed by the audio playback system according to the first embodiment of the present invention.

As shown in FIG. 2, the handheld device 11 comprises a first transmitting terminal controller 110. The first transmitting terminal controller 110 uses a high frequency sound wave signal as a carrier wave in order to convert the control message into the modulated sound wave signal. In this embodiment, the first transmitting terminal controller 110 comprises the first speaker 111, a first sound wave signal generator 112, and an instruction receiver 114. The first sound wave signal generator 112 comprises a first encoder 1121, a first audio modulator 1122, and a carrier wave generator 1123. The digital stereo set 12 comprises a first receiving terminal controller 120 for restoring the modulated sound wave signal to the control message. The first receiving terminal controller 120 comprises the first microphone 1211 and a first sound wave signal reader 123. The first sound wave signal reader 123 comprises a first pre-processor 1231, a first audio demodulator 1232, and a first message interpreter 1233.

When the user wants to use the handheld device 11 to control the digital stereo set 12, the user may firstly select and open an application program (APP) from the handheld device 11. The application program may be built in the handheld device 11. Alternatively, the application program may be downloaded to the handheld device 11 by the user, and then installed in the handheld device 11.

After the application program is opened, a user interface (UI) 113 is shown on a display screen 115. As shown in FIG. 3, the user interface 113 comprises a first playback control instruction 1131, a second playback control instruction 1132, a third playback control instruction 1133, and a fourth playback control instruction 1134. In an embodiment, the first playback control instruction 1131 denotes "an instruction of starting playback from previous pause", the second playback control instruction 1132 denotes "an instruction of random playback", the third playback control instruction 1133 denotes "an instruction of playing a first playing file list", and the fourth playback control instruction 1134 denotes "an instruction of establishing a playing file list". It is noted that the above instructions are presented herein for purpose of illustration and description only. However, those skilled in the art will readily observe that numerous modifications and alterations of the type of the user interface 113 and the playback control instructions may be made according to the practical requirements.

Moreover, each playback control instruction has a corresponding binary instruction code. According to the default settings, the binary instruction code can be identified and executed by the digital stereo set 12. For example, in this embodiment, a binary instruction code corresponding to the first playback control instruction 1131 is "11011110", a binary instruction code corresponding to the second playback control instruction 1132 is "01010010", a binary instruction code corresponding to the third playback control instruction 1133 is "11011101", and a binary instruction code corresponding to the fourth playback control instruction 1134 is "00001111". It is noted that the binary instruction codes corresponding to the respective playback control instructions are presented herein for purpose of illustration and description only.

Then, the user may select one or more binary instruction codes from the user interface 113. If the first playback control instruction 1131 (i.e. the instruction of starting playback from previous pause) is selected by the user and the first playback control instruction 1131 is confirmed to be executed, a binary instruction code A corresponding to a control message X which is generated upon confirmation of the selected first playback control instruction 1131 will be transmitted from the instruction receiver 114 to the first encoder 1121. At the same time, a prompt message is shown on the user interface 113 of the handheld device 11 to notify the user of allowing the first speaker 111 to face and approach the first microphone 1211 of the digital stereo set 12 in order to send the control message X.

In some situations, one digital stereo set 12 may be controlled by plural handheld devices. For executing a control action corresponding to a specified handheld device (i.e. a personalized control action), the digital stereo set 12 should realize which handheld device sends the control message X. Consequently, in this embodiment, the control message X contains the first playback control instruction 1131 and a handheld device identification code of the handheld device 11. In other words, a binary instruction code A1 corresponding to the first playback control instruction 1131 is transmitted from the instruction receiver 114 to the first encoder 1121, and a binary instruction code A2 corresponding to the handheld device identification code of the handheld device 11 is also transmitted from the instruction receiver 114 to the first encoder 1121.

In this embodiment, the handheld device identification code may be a code name that is set by the user (e.g. a code name "D"), but is not limited thereto. Alternatively, the handheld device identification code may be an IMEI code or a MAC address of the handheld device 11. In this embodiment, the binary instruction code A2 corresponding to the handheld device identification code of the handheld device 11 is "01000100".

Next, the binary instruction codes A1 and A2 are encoded by first encoder 1121, and thus a first pulse signal B is obtained. The contents of the first pulse signal B will be illustrated as follows. As shown in FIG. 4, a 2 ms-width high voltage level signal and a successive 2 ms-width low voltage level signal are collectively defined as a binary code "0"; and a 4 ms-width high voltage level signal and a successive 2 ms-width low voltage level signal are collectively defined as a binary code "1". Consequently, as shown in FIG. 4, the binary instruction code A2 corresponding to the handheld device identification code is converted into a handheld device identification signal B2 according to the above definitions, and the binary instruction code A1 corresponding to the first playback control instruction 1131 is converted into a playback control instruction signal B1 according to the above definitions.

Moreover, for clearly defining the ranges of the binary instruction codes A1 and A2, the first pulse signal B further comprises a start signal B3 prior to the playback control instruction signal B1 and another start signal B3 prior to the handheld device identification signal B2; and the first pulse signal B further comprises a termination signal B4 posterior to the playback control instruction signal B1 and another termination signal B4 posterior to the handheld device identification signal B2.

Moreover, for clearly distinguishing the binary instruction codes A1 and A2 from each other, the first pulse signal B further comprises a spacing signal B5 between the playback control instruction signal B1 and the handheld device identification signal B2. In other words, the first pulse signal B of this embodiment is composed of the playback control instruction signal B1, the handheld device identification signal B2, the start signal B3, the termination signal B4 and the spacing signal B5.

In this embodiment, an 8 ms-width high voltage level signal and a successive 2 ms-width low voltage level signal are collectively defined as the start signal B3; a 6 ms-width high voltage level signal and a successive 4 ms-width low voltage level signal are collectively defined as the termination signal B4; and a 2 ms-width high voltage level signal and a successive 20 ms-width low voltage level signal are collectively defined as the spacing signal B5.

The carrier wave generator 1123 is used for generating a high frequency sound wave signal. In this embodiment, the frequency of the high frequency sound wave signal is in a range between 12 KHz and 20 KHz. The frequency of the high frequency sound wave signal is within the human hearing frequency range, and is a sound wave frequency that can be emitted by the handheld device 11.

Next, the first pulse signal B and the high frequency sound wave signal are transmitted to the first audio modulator 1122 together. By the first audio modulator 1122, the first pulse signal B is modulated with the high frequency sound wave signal, so that a first modulation signal is generated.

In an embodiment, after the high voltage level signal of the first pulse signal B is modulated into the signal with a frequency of 18 KHz, the first modulation signal is generated. Alternatively, in some other embodiments, after the high voltage level signal of the first pulse signal B is modulated into the signal with a frequency of 15 KHz and the low voltage level signal of the first pulse signal B is modulated into the signal with a frequency of 12 KHz, the first modulation signal is generated.

It is noted that the above encoding method of FIG. 4 is presented herein for purpose of illustration and description only. That is, the encoding method of the present invention is not restricted.

Next, the first modulation signal is transmitted to the first speaker 111 to drive vibration of a vibration film of the first speaker 111. Consequently, the first speaker 111 sends a first modulated sound wave signal P while using air as a transmission medium.

When the first modulated sound wave signal P is received by the first microphone 1211, the first microphone 1211 generates a corresponding first electric signal. Next, the first electric signal is transmitted to the first pre-processor 1231. In this embodiment, the first pre-processor 1231 is a filter or an amplifier. The filter is used for removing the undesired component of the first electric signal or strengthening the desired component of the first electric signal. The amplifier is used for amplifying the weak signal. Regardless of whether the first pre-processor 1231 is the filter or the amplifier, the purpose of the first pre-processor 1231 is to reduce interference and compensate loss. Consequently, the first electric signal is restored to the first modulation signal more completely. Moreover, the first pre-processor 1231 may further comprise an automatic gain control circuit.

After the first electric signal is adjusted by the first pre-processor 1231, the adjusted first electric signal is transmitted to the first audio demodulator 1232. By the first audio demodulator 1232, the first electric signal is restored to the undecoded first pulse signal B. Afterwards, the undecoded first pulse signal B is transmitted to the first message interpreter 1233. By the first message interpreter 1233, the first pulse signal B is restored to the binary instruction code A2 corresponding to the handheld device identification code and the binary instruction code A1 corresponding to the first playback control instruction 1131 according to the above encoding rule of the first encoder 1121. Consequently, the control message X is obtained according to the binary instruction codes A1 and A2.

In case that the first pulse signal B is modulated with the high frequency sound wave signal by the first audio modulator 1122 according to an amplitude modulation method, the first audio demodulator 1232 is a detector. Whereas, in case that the first pulse signal B is modulated with the high frequency sound wave signal by the first audio modulator 1122 according to a frequency modulation method, the first audio demodulator 1232 is a phase-locked loop detector.

According to the control message X, the digital stereo set 12 recognizes that the handheld device 11 requests to start playback from previous pause. Since the usage history of each device is recorded in the digital stereo set 12, the digital stereo set 12 may search the playback history of the handheld device 11 from its database and start playback from previous pause of the handheld device 11.

On the other hand, if the second playback control instruction 1132 (i.e. the instruction of random playback) and the third playback control instruction 1133 (i.e. the instruction of playing the first playing file list) are selected from the user interface 113 by the user, after the binary instruction code A2 corresponding to the handheld device identification code, a binary instruction code corresponding to the second playback control instruction 1132 and a binary instruction code corresponding to the third playback control instruction 1133 are received by the digital stereo set 12, the first playing file list corresponding to the handheld device 11 is selected from the database and the audio files of the first playing file list are randomly played.

On the other hand, if only the second playback control instruction 1132 (i.e. the instruction of random playback) is selected from the user interface 113 by the user, only the binary instruction code corresponding to the second playback control instruction 1132 is transmitted from the handheld device 11 to the digital stereo set 12. In other words, it is not necessary to transmit the handheld device identification code of the handheld device 11, but the audio files in the database can be randomly played by the digital stereo set 12.

On the other hand, if the fourth playback control instruction 1134 (i.e. the instruction of establishing a playing file list) is selected from the user interface 113 by the user, it is necessary for the user to previously set the contents of the playing file list through the user interface 113 of the handheld device 11. After the binary instruction code A2 corresponding to the handheld device identification code, a binary instruction code corresponding to the fourth playback control instruction 1134 and a binary instruction code corresponding to the playing file list are received by the digital stereo set 12, the playing file list corresponding to the handheld device 11 is established in the database of the digital stereo set 12.

From the above discussions about the audio playback system 1, the first modulated sound wave signal P from the first speaker 111 is used to transmit the control message X in order to control the digital stereo set 12 to execute the corresponding control action. Moreover, in the audio playback system 1 of this embodiment, the control message X may be transmitted from the existing speaker of the handheld device 11 to the digital stereo set 12. Since it is not necessary to transmit the control message X by the wireless communication technology, the drawbacks encountered from the above-mentioned radio frequency communication technology will be solved. Moreover, the purpose of executing the personalized control action is achievable by transmitting the handheld device identification code.

By the way, the handheld device 11 of the present invention may transmit other control messages to the digital stereo set 12. According to other control messages from the handheld device 11, the digital stereo set 12 may execute other control actions (e.g. play, pause, previous, next, fast forward, fast reverse, and the like).

Figure 5:
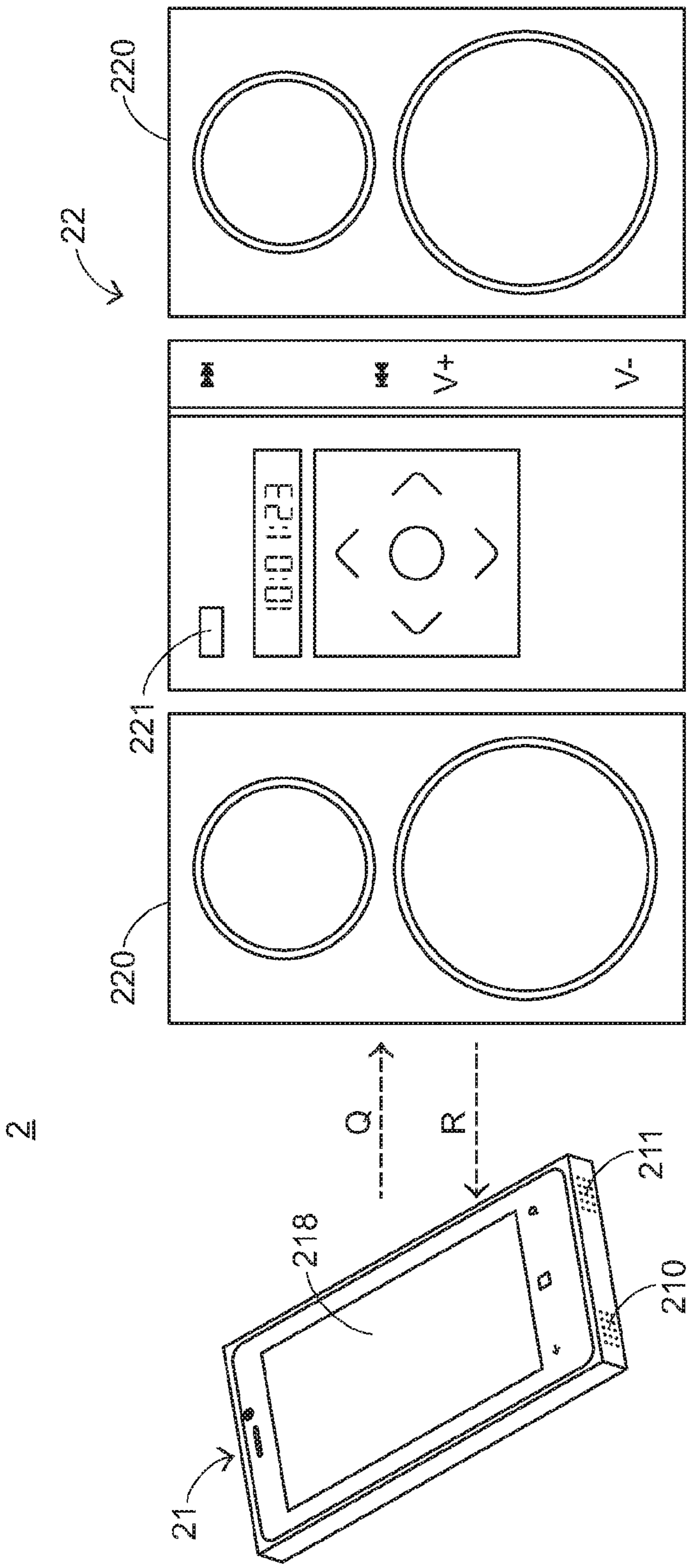
FIG. 5 schematically illustrates the architecture of an audio playback system according to a second embodiment of the present invention.
Figure 6:
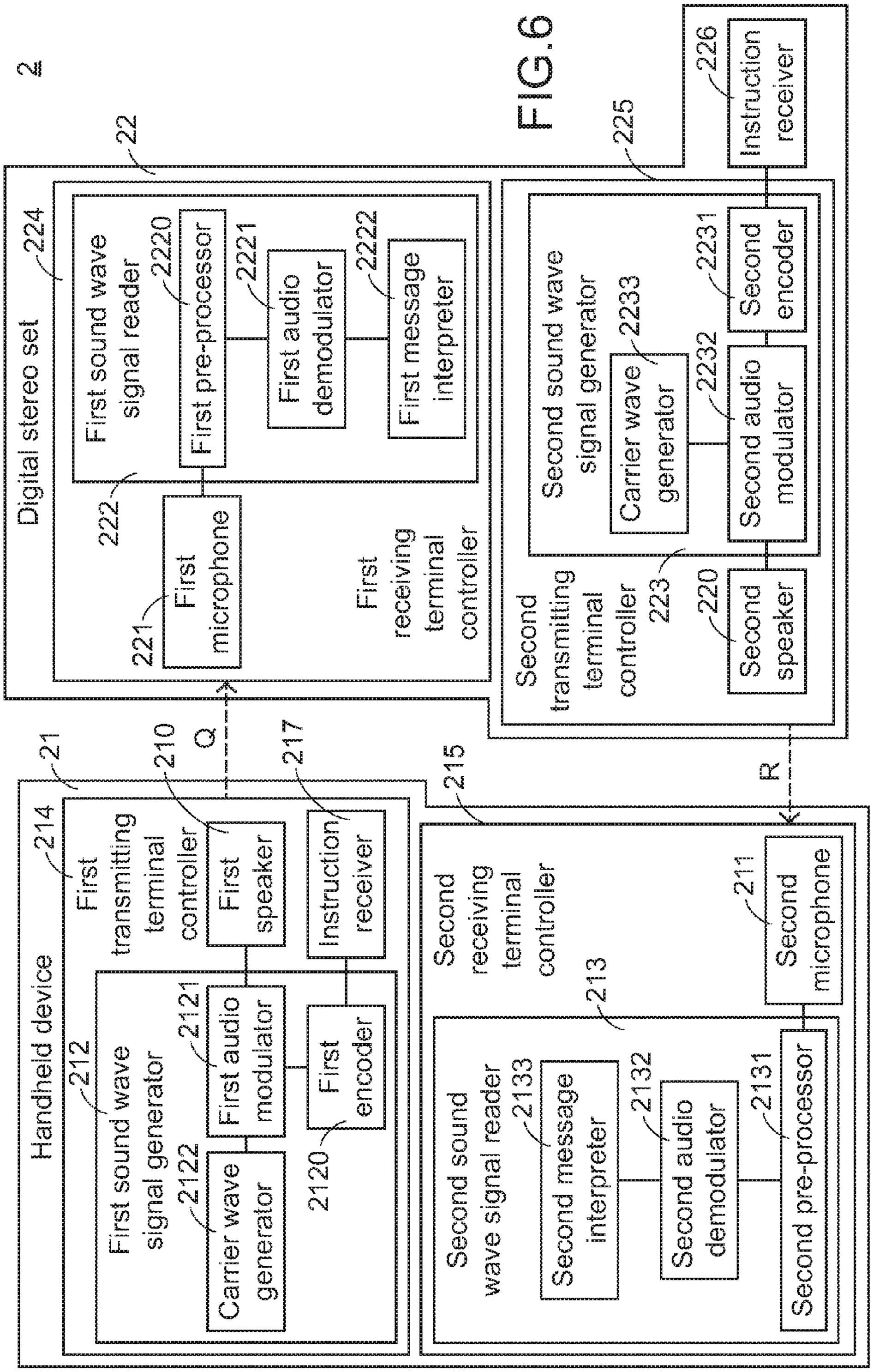
FIG. 6 is a schematic functional block illustrating the audio playback system according to the second embodiment of the present invention.

Hereinafter, an audio playback system according to a second embodiment of the present invention will be illustrated with reference to FIGS. 5 and 6. FIG. 5 schematically illustrates the architecture of an audio playback system according to a second embodiment of the present invention. FIG. 6 is a schematic functional block illustrating the audio playback system according to the second embodiment of the present invention.

As shown in FIGS. 5 and 6, the audio playback system 2 comprises a handheld device 21 and a digital stereo set 22. In this embodiment, the handheld device 21 comprises a first transmitting terminal controller 214 and a second receiving terminal controller 215. The first transmitting terminal controller 214 comprises a first speaker 210, a first sound wave signal generator 212, and an instruction receiver 217. The second receiving terminal controller 215 comprises a second microphone 211 and a second sound wave signal reader 213.

The digital stereo set 22 comprises a first receiving terminal controller 224 and a second transmitting terminal controller 225. The first receiving terminal controller 224 comprises a first microphone 221 and a first sound wave signal reader 222. The second transmitting terminal controller 225 comprises a second speaker 220, a second sound wave signal generator 223, and an instruction receiver 226.

The first sound wave signal generator 212 of the handheld device 21 comprises a first encoder 2120, a first audio modulator 2121, and a carrier wave generator 2122. The second sound wave signal reader 213 of the handheld device 21 comprises a second pre-processor 2131, a second audio demodulator 2132, and a second message interpreter 2133.

The first sound wave signal reader 222 of the digital stereo set 22 comprises a first pre-processor 2220, a first audio demodulator 2221, and a first message interpreter 2222. The second sound wave signal generator 223 of the digital stereo set 22 comprises a second encoder 2231, a second audio modulator 2232, and a carrier wave generator 2233.

In this embodiment, the first speaker 210 is located at a bottom of the handheld device 21 and has a function of playing audio contents, the second speaker 220 is an audio box of the digital stereo set 22, and the second microphone 211 is located at the bottom of the handheld device 21 and has a function of receiving sound. Moreover, an example of the second microphone 211 includes but is not limited to a dynamic microphone, a capacitive microphone, an electret condenser microphone or a microelectromechanical systems (MEMS) microphone.

The audio playback system 2 of this embodiment has the control functions of the audio playback system 1 of the first embodiment. Furthermore, a pairing relation between the handheld device 21 and the digital stereo set 22 can be established by the first speaker 210, the first sound wave signal generator 212, the second microphone 211 and the second sound wave signal reader 213 of the handheld device 21 and the first microphone 221, the first sound wave signal reader 222, the second speaker 220 and the second sound wave signal generator 223 of the digital stereo set 22. After the pairing relation is established, data can be exchanged between the handheld device 21 and the digital stereo set 22, and a reverse control function is achievable. A process of establishing the pairing relation will be illustrated in more details as follows.

Figure 7:
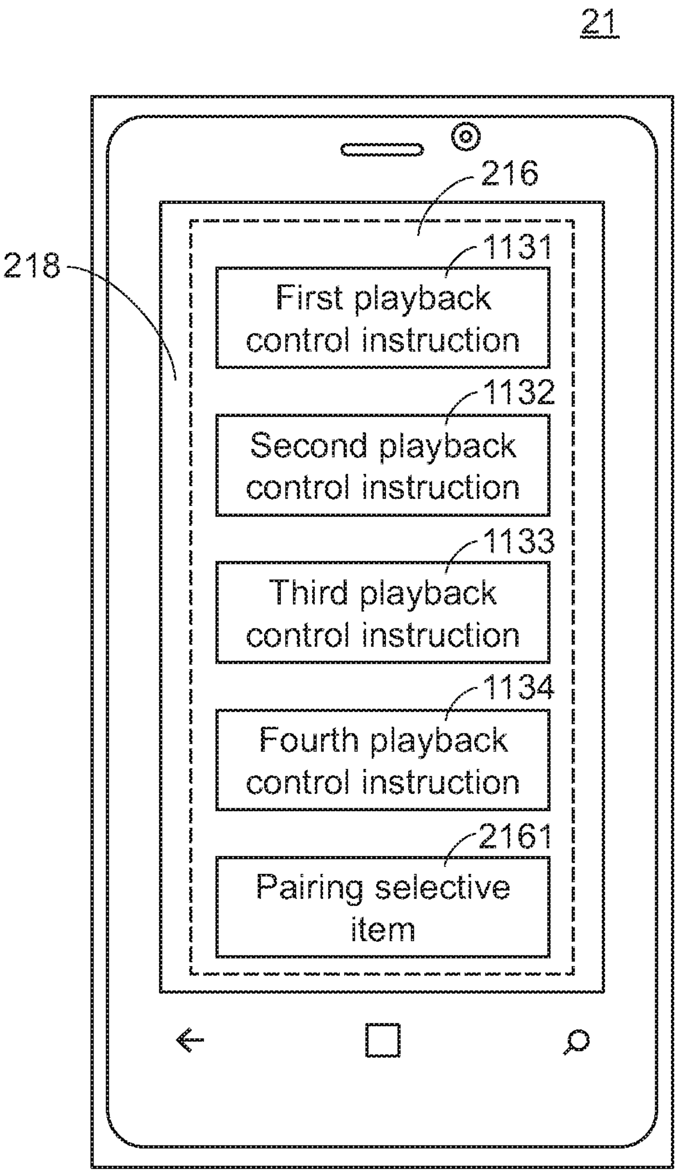
FIG. 7 schematically illustrates a user interface of the audio playback system according to the second embodiment of the present invention.

Please refer to FIGS. 5~7. FIG. 7 schematically illustrates a user interface of the audio playback system according to the second embodiment of the present invention. For pairing the handheld device 21 with the digital stereo set 22, the user may firstly select and open an application program (APP) from the handheld device 21. The application program may be built in the handheld device 21. Alternatively, the application program may be downloaded to the handheld device 21 by the user, and then installed in the handheld device 21.

After the application program is opened, a user interface 216 is shown on a display screen 218. The user interface 216 at least comprises a pairing selective item 2161. After the pairing selective item 2161 is selected by the user, the handheld device 21 may prompt the user to have the first speaker 210 approach the first microphone 221 of the digital stereo set 22.

Moreover, after the pairing selective item 2161 is selected, a control message is correspondingly generated. The control message is transmitted from the instruction receiver 217 to the first sound wave signal generator 212. By the first sound wave signal generator 212, the control message is converted into a first pulse signal, and then the first pulse signal is converted into a first modulation signal. In response to the first modulation signal, the first speaker 210 is driven to output a first modulated sound wave signal Q. In this embodiment, the control message is a paring instruction. The first pulse signal comprises the start signal B3, the termination signal B4, and a pairing instruction signal which is obtained by encoding a binary instruction code corresponding to the pairing instruction. Moreover, the process of converting the control message into the first modulated signal by the first sound wave signal generator 212 is similar to the process of converting the control message X into the first modulated signal by the first sound wave signal generator 112 of the first embodiment, and is not redundantly described herein.

After the first modulated sound wave signal Q is received by the first microphone 221 of the digital stereo set 22, the first modulated sound wave signal Q is restored to the control message by the first sound wave signal reader 222. The process of restoring the first modulated sound wave signal Q to the control message by the first sound wave signal reader 222 is similar to the process of restoring the first modulated sound wave signal P to the control message X by the first sound wave signal reader 123, and is not redundantly described herein.

Next, according to the control message (i.e. the pairing instruction), the instruction receiver 226 of the digital stereo set 22 sends a stereo device identification code to the second encoder 2231 and the second audio modulator 2232. Consequently, the stereo device identification code is converted into a second pulse signal, and the second pulse signal is then converted into a second modulation signal. The second modulation signal is transmitted to the second speaker 220. In response to the second modulation signal, the second speaker 220 is driven to output a second modulated sound wave signal R. In this embodiment, the stereo device identification code is a built-in paring password (e.g. 8888, 0000 or 1111) of the digital stereo set 22 for pairing. The second pulse signal comprises the start signal B3, the termination signal B4, and a pairing instruction signal which is obtained by encoding the binary instruction code corresponding to the stereo device identification code The operations of the second encoder 2231 and the second audio modulator 2232 are similar to the operations of the first encoder 1121 and the first audio modulator 1122 of the first embodiment, and are not redundantly described herein.

After the second modulated sound wave signal R is received by the second microphone 211, the second microphone 211 generates a corresponding second electric signal in response to the second modulated sound wave signal R. After the second electric signal is adjusted by the second pre-processor 2131 of the second sound wave signal reader 213, the interference of the second electric signal is reduced. Then, the second electric signal is restored to the second pulse signal by the second audio demodulator 2132. Afterwards, the second pulse signal is restored to the stereo device identification code by the second message interpreter 2133. In this embodiment, the second pre-processor 2131 is an audio processing chip of the handheld device 21, wherein the audio processing chip includes an amplifier and an analog-to-digital converter. Moreover, the second audio demodulator 2132 and the second message interpreter 2133 may be software that is built in the handheld device 21 or additionally installed in the handheld device 21.

The operations of the second pre-processor 2131, the second audio demodulator 2132 and the second message interpreter 2133 are similar to the operations of the first preprocessor 1231, the audio demodulator 1232 and the first message interpreter 1233 of the first embodiment, and are not redundantly described herein.

After the stereo device identification code is acquired by the handheld device 21, a user code of the digital stereo set 22 may be shown on the user interface 216 of the display screen 218. After the user code of the digital stereo set 22 is selected by the user, the paring process is completed by the handheld device 21. From now on, data can be transmitted between the handheld device 21 and the digital stereo set 22. Moreover, the handheld device 21 may issue a sound or any other information to notify the digital stereo set 22 that the pairing process is completed.

From the above descriptions about the audio playback system of the present invention, the speaker and the microphone are used to achieve the purpose of transmitting the control message between the handheld device and the digital stereo set. Moreover, the purpose of executing the personalized control action is achievable by transmitting the handheld device identification code. Consequently, the audio playback system of the present invention is capable of eliminating the drawbacks of the above-mentioned wireless communication technology. Moreover, the audio playback system of the present invention can quickly and conveniently control the corresponding control action of the digital stereo set, especially the personalized control action. Moreover, the audio playback system of the present invention can establish the pairing relation between the handheld device and the digital stereo set through sound wave communication. In comparison with the wireless communication technology, the pairing process used in the audio playback system of the present invention is simplified and has less possibility of causing erroneous pairing action.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An audio playback system, comprising:

a handheld device comprising a first transmitting terminal controller, wherein the first transmitting terminal controller comprises:

a first speaker; and a first sound wave signal generator for converting a control message into a first modulation signal, and transmitting the first modulation signal to the first speaker, thereby controlling the first speaker to generate a first modulated sound wave signal; and a digital stereo set comprising a host and a sound box for playing a digital audio file, wherein the digital stereo set further comprises a first receiving terminal controller, and the first receiving terminal controller comprises:

a first microphone for receiving the first modulated sound wave signal; and a first sound wave signal reader for restoring the first modulated sound wave signal to the control message, wherein after the control message is received by the digital stereo set, the digital stereo set performs a corresponding control action according to the control message.

2. The audio playback system according to claim 1, wherein the first sound wave signal generator of the handheld device comprises:

a first encoder for converting the control message into a first pulse signal;

a carrier wave generator for generating a high frequency sound wave signal; and a first audio modulator for modulating the first pulse signal with the high frequency sound wave signal, thereby generating the first modulation signal.

3. The audio playback system according to claim 2, wherein a frequency of the high frequency sound wave signal is in a range between 12 KHz and 20 KHz.

4. The audio playback system according to claim 2, wherein the first sound wave signal reader of the digital stereo set comprises:

a first pre-processor for adjusting a first electric signal to reduce interference, wherein the first electric signal is generated when the first modulated sound wave signal is received by the first microphone;

a first audio demodulator for restoring the first electric signal to the first pulse signal; and a first message interpreter for restoring the first pulse signal to the control message.

5. The audio playback system according to claim 4, wherein the first pre-processor is a filter or an amplifier.

6. The audio playback system according to claim 1, wherein the handheld device further comprises a display screen for providing a user interface, wherein via the user interface, the control message is selectively transmitted by a user.

7. The audio playback system according to claim 1, wherein the handheld device is a smart phone or a tablet personal computer.

8. The audio playback system according to claim 1, wherein the control message contains at least one playback control instruction, or the control message contains at least one playback control instruction and a handheld device identification code.

9. The audio playback system according to claim 1, wherein the control message is a pairing instruction.

10. The audio playback system according to claim 9, wherein the digital stereo set further comprises a second transmitting terminal controller, and the handheld device further comprises a second receiving terminal controller, wherein the second transmitting terminal controller comprises a second speaker and a second sound wave signal generator, wherein the second sound wave signal generator is configured for converting a stereo device identification code of the digital stereo set into a second modulation signal, and transmitting the second modulation signal to the second speaker, thereby controlling the second speaker to generate a second modulated sound wave signal, wherein the second receiving terminal controller comprises a second microphone for receiving the second modulated sound wave signal, and a second sound wave signal reader for restoring the second modulated sound wave signal to the stereo device identification code, wherein after the control message is received by the digital stereo set, the stereo device identification code is converted into the second modulation signal by the second transmitting terminal controller.

11. The audio playback system according to claim 10, wherein the second sound wave signal generator of the digital stereo set comprises:

a second encoder for converting the stereo device identification code into the second pulse signal;

a carrier wave generator for generating a high frequency sound wave signal; and a second audio modulator for modulating the second pulse signal with the high frequency sound wave signal, thereby generating the second modulation signal.

12. The audio playback system according to claim 11, wherein the second sound wave signal reader of the handheld device comprises:

a second pre-processor for adjusting a second electric signal to reduce interference, wherein the second electric signal is generated when the second modulated sound wave signal is received by the second microphone;

a second audio demodulator for restoring the second electric signal to the second pulse signal; and a second message interpreter for restoring the second pulse signal to the stereo device identification code.

13. The audio playback system according to claim 10, wherein the handheld device further comprises a display screen for providing a user interface, wherein via the user interface, a pairing process is selectively activated by a user.

* * * * *